US00PP29199P2

(12) United States Plant Patent
Smit

(10) Patent No.: US PP29,199 P2
(45) Date of Patent: Apr. 3, 2018

(54) ***ECHEVERIA* PLANT NAMED 'EC-ECH-03'**

(50) Latin Name: ***Echeveria* hybrid**
Varietal Denomination: EC-ECH-03

(71) Applicant: Obed Jacob Smit, Sappemeer (NL)

(72) Inventor: Obed Jacob Smit, Sappemeer (NL)

(73) Assignee: Eden Collection B.V., Sappemeer (NL)

( * ) Notice: Subject to any disclaimer, the term of this patent is extended or adjusted under 35 U.S.C. 154(b) by 60 days.

(21) Appl. No.: 15/330,376

(22) Filed: Sep. 12, 2016

(51) Int. Cl.
*A01H 5/02* (2018.01)
*A01H 5/12* (2018.01)

(52) U.S. Cl.
USPC ..... Plt./373
CPC ..... *A01H 5/12* (2013.01)

(58) Field of Classification Search
USPC ..... Plt./373
See application file for complete search history.

*Primary Examiner* — Keith O Robinson

(57) ABSTRACT

A new cultivar of *Echeveria* plant named 'EC-ECH-03' that is characterized by large glossy leaves that are brown-purple in color with red margins.

1 Drawing Sheet

Botanical classification: *Echeveria* hybrid.
Variety denomination: 'EC-ECH-03'.

BACKGROUND OF THE INVENTION

The present invention relates to a new and distinct cultivar of *Echeveria* plant botanically known as *Echeveria* hybrid and hereinafter referred to by the cultivar name 'EC-ECH-03'.

'EC-ECH-03' originated from the crossing of the female or seed parent, an unnamed *Echeveria gigantea* cultivar and the male or pollen parent, *Echeveria* 'Black Prince' (not patented). The crossing was conducted in 2013 in Sappemeer, Netherlands. The resulting seeds were subsequently planted and grown. The cultivar 'EC-ECH-03' was selected by the inventor in 2014 in a controlled environment as a single plant within the progeny of the stated cross in a cultivated area of Sappemeer, Netherlands.

Asexual reproduction of the new cultivar 'EC-ECH-03' first occurred by leaf cuttings in 2014 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Echeveria* cultivar 'EC-ECH-03'. These traits in combination distinguish 'EC-ECH-03' as a new and distinct cultivar apart from other existing varieties of *Echeveria* known by the inventor.

1. *Echeveria* 'EC-ECH-03' exhibits large brown-purple leaves.
2. *Echeveria* 'EC-ECH-03' exhibits red colored margins.
2. *Echeveria* 'EC-ECH-03' exhibits glossy leaves.

The closest comparison cultivars are *Echeveria* 'Red Prince' (not patented) and *Echeveria* 'Giant Blue' (not patented) 'EC-ECH-03' is distinguishable from 'Red Prince' by the following characteristics:

1. *Echeveria* 'EC-ECH-03' exhibits brown-purple leaves. In comparison, the leaves of 'Red Prince' are purple-green.
2. *Echeveria* 'EC-ECH-03' exhibits leaves that are larger in width than the leaves of 'Red Prince'.
3. *Echeveria* 'EC-ECH-03' exhibits a smaller number of leaves than the number of leaves of 'Red Prince'.
4. *Echeveria* 'EC-ECH-03' exhibits a larger overall plant width than the overall plant width of 'Red Prince'.

'EC-ECH-03' is distinguishable from 'Giant Blue' by the following characteristics:

1. *Echeveria* 'EC-ECH-03' exhibits brown-purple leaves. In comparison, the leaves of 'Giant Blue' are blue.
2. *Echeveria* 'EC-ECH-03' exhibits leaves that are slightly concave in aspect. In comparison, the leaves of 'Giant Blue' are curled.

'EC-ECH-03' is distinguishable from the female parent plant, an unnamed *Echeveria gigantea* cultivar, by the following characteristics:

1. *Echeveria* 'EC-ECH-03' exhibits brown-purple leaves. In comparison, the leaves of the female parent plant are grey-green.
2. *Echeveria* 'EC-ECH-03' exhibits a smaller overall plant height than the overall plant height of the female parent plant.

'EC-ECH-03' is distinguishable from the male parent plant, *Echeveria* 'Black Prince' by the following characteristics:

1. *Echeveria* 'EC-ECH-03' exhibits brown-purple leaves. In comparison, the leaves of 'Black Prince' are dark purple.
2. *Echeveria* 'EC-ECH-03' exhibits leaves that are shorter in length and more rounded in shape than the leaves of 'Black Prince'.
3. *Echeveria* 'EC-ECH-03' exhibits a smaller number of leaves than the number of leaves of 'Black Prince'.
4. *Echeveria* 'EC-ECH-03' exhibits leaves with red margins. In comparison, the leaves and margins of 'Black Prince' are the same dark purple color.

BRIEF DESCRIPTION OF THE DRAWING

The accompanying photographs illustrate the distinguishing traits of *Echeveria* 'EC-ECH-03'.

FIG. 1 shows an overall view of a 25 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Echeveria* cultivar named 'EC-ECH-03'. Data was collected in Sappemeer, Netherlands from 25 week old plants grown in a glass greenhouse in 12 cm. diameter containers. The time of year was Winter and the temperature range was 18-25 degrees Centigrade during the day and 12-18 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'EC-ECH-03' has not been tested under all possible conditions and phenotypic differences may be observed with variations in environmental, climatic, and cultural conditions, however, without any variance in genotype.

Botanical classification: *Echeveria* hybrid 'EC-ECH-03'.
Annual or perennial: Perennial.
Parentage: 'EC-ECH-03' is a hybrid of the female parent, an unnamed *Echeveria gigantea* cultivar and the male or pollen parent, *Echeveria* 'Black Prince'.
Plant type: Pot plant.
Plant shape: Basal rosette with a short stem.
Suitable container size: 7 cm. pots or larger.
Plant height: 7.1 cm.
Plant width: 15.3 cm.
Vigor: Moderate.
Low Temperature Tolerance: 5° Centigrade.
High Temperature Tolerance: 40° Centigrade.
Propagation: Leaf cuttings.
Time to initiate roots (summer): 7 days at 25° C.
Time to initiate roots (winter): 14 days at 18° C.
Time to produce a rooted cutting: Leaf cuttings are placed directly into growing container.
Growth rate: Moderate.
Crop time: Approximately 20 to 25 weeks from June to November in Sappemeer, Netherlands.
Root system: Fibrous.
Root color: N155.
Plant fragrance: None.

Stem:
- *Number of stems.*—1.
- *Stem dimensions.*—3.8 cm. in length and 1.0 cm. in width.
- *Internode length.*—0.15 cm.
- *Stem shape.*—Rounded.
- *Stem texture.*—Smooth.
- *Stem angle.*—Vertical, zero degrees.
- *Stem strength.*—Strong.
- *Stem pubescence.*—Absent.
- *Stem color* (*young*).—145A to 145C.
- *Stem color* (*mature*).—182D.
- *Internode color.*—182D.

Foliage:
- *Leaf arrangement.*—Basal rosette.
- *Compound or single.*—Single.
- *Quantity of leaves per plant.*—Average 20.
- *Leaf shape.*—Broad spathulate.
- *Leaf aspect.*—Flat to moderately carinate.
- *Leaf apex.*—Broad retuse with a small acute outer tip.
- *Leaf base.*—Attenuate.
- *Leaf dimensions.*—7.0 cm. in length and 6.8 cm. in width.
- *Leaf thickness.*—0.35 cm.
- *Texture.*—Glabrous both surfaces, succulent.
- *Pubescence.*—Absent.
- *Leaf margin.*—Entire.
- *Venation pattern.*—None visible.
- *Young leaf color* (*upper surface*).—NN137A, tinged N186C, base 141A, margins 182A, covered with thin waxy layer 189A to 189B.
- *Young leaf color* (*lower surface*).—147B to 147C, tinged 187C, base 143A, margins 182A, covered with thin waxy layer 189A to 189B.
- *Mature leaf color* (*upper surface*).—N200A, tinged 148A, margins 176A, covered with thin waxy layer 188A.
- *Mature leaf color* (*lower surface*).—Between N200A and N200B, margins 176A, covered with thin waxy layer 188A.
- *Leaf attachment.*—Sessile.

Flower: 'EC-ECH-03' has not produced flowers to date.
Fruit and seed: 'EC-ECH-03' has not produced fruit or seed to date.
Disease and pest resistance: Disease and pest resistance has not been observed.

The invention claimed is:

1. A new and distinct variety of *Echeveria* plant named 'EC-ECH-03' as described and illustrated.

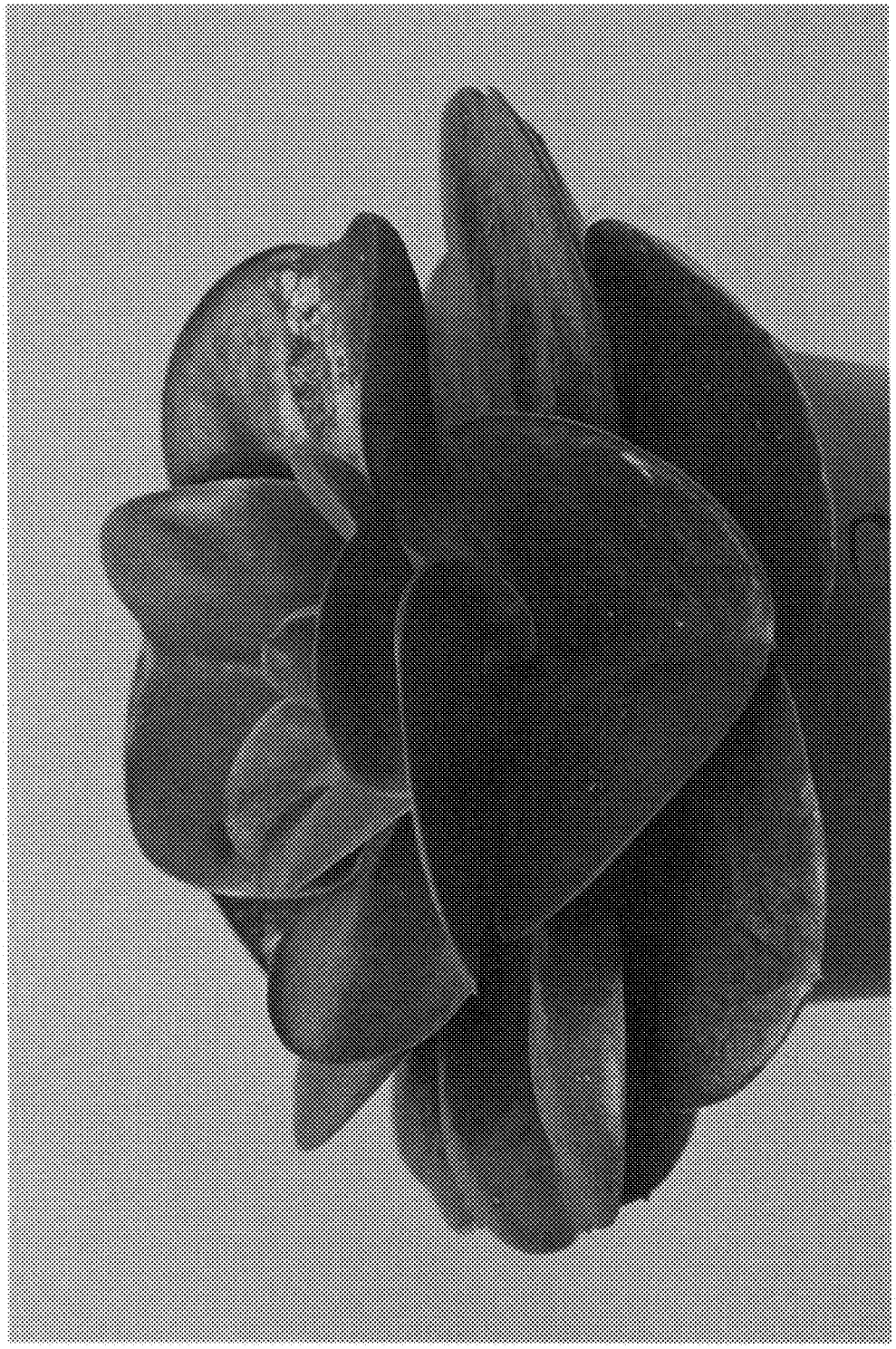

* * * * *